(12) United States Patent
Benz et al.

(10) Patent No.: US 11,717,564 B2
(45) Date of Patent: *Aug. 8, 2023

(54) ITERATIVE DISCOVERY OF NEOEPITOPES AND ADAPTIVE IMMUNOTHERAPY AND METHODS THEREFOR

(71) Applicant: NANTOMICS, LLC, Culver City, CA (US)

(72) Inventors: Stephen Charles Benz, Culver City, CA (US); Kayvan Niazi, Culver City, CA (US); Patrick Soon-Shiong, Culver City, CA (US); Andrew Nguyen, Culver City, CA (US)

(73) Assignee: NantOmics, LLC, Culver City, CA (US)

( * ) Notice: Subject to any disclaimer, the term of this patent is extended or adjusted under 35 U.S.C. 154(b) by 601 days.

This patent is subject to a terminal disclaimer.

(21) Appl. No.: 16/713,680

(22) Filed: Dec. 13, 2019

(65) Prior Publication Data

US 2020/0113985 A1 Apr. 16, 2020

Related U.S. Application Data

(63) Continuation of application No. 15/291,911, filed on Oct. 12, 2016, now Pat. No. 10,532,089.
(Continued)

(51) Int. Cl.
*A61K 39/00* (2006.01)
*G01N 33/574* (2006.01)
(Continued)

(52) U.S. Cl.
CPC .... *A61K 39/0011* (2013.01); *G01N 33/57484* (2013.01); *G16B 20/20* (2019.02);
(Continued)

(58) Field of Classification Search
None
See application file for complete search history.

(56) References Cited

U.S. PATENT DOCUMENTS 7,473,532 B2  1/2009  Darfler et al.
10,532,089 B2 1/2020 Benz et al.
(Continued)

FOREIGN PATENT DOCUMENTS

AU 2016339022 B2 9/2020
CA   3 003 305 A1 4/2017
(Continued)

OTHER PUBLICATIONS

Carreno BM et al., "Supplementary Materials for A dendritic cell vaccine increases the breadth and diversity of melanoma neoantigen-specific T cells", Science, Apr. 2, 2015, vol. 348, No. 6236,p. p. 1-9., XP055586846, ISSN: 0036-8075, DOI: 10.1126/science.aaa3828.
(Continued)

*Primary Examiner* — Lori A. Clow
(74) *Attorney, Agent, or Firm* — Martin Fessenmaier; Umberg Zipser LLP

(57) ABSTRACT

Contemplated cancer treatments comprise recursive analysis of patient-, cancer-, and location-specific neoepitopes from various biopsy sites of a patient after treatment or between successive rounds of immunotherapy and/or chemotherapy to inform further immunotherapy. Recursive analysis preferably includes various neoepitope attributes to so identify treatment relevant neoepitopes.

20 Claims, 1 Drawing Sheet

Related U.S. Application Data

(60) Provisional application No. 62/240,482, filed on Oct. 12, 2015.

(51) Int. Cl.

| | | |
|---|---|---|
| *G16H 20/00* | (2018.01) | |
| *G16H 20/40* | (2018.01) | |
| *G16H 70/60* | (2018.01) | |
| *G16B 20/20* | (2019.01) | |
| *G16B 30/10* | (2019.01) | |
| *G16B 20/00* | (2019.01) | |

(52) U.S. Cl.
CPC .............. *G16B 30/10* (2019.02); *G16H 20/00* (2018.01); *G16H 20/40* (2018.01); *G16H 70/60* (2018.01); *G01N 2800/52* (2013.01); *G16B 20/00* (2019.02)

(56) References Cited

U.S. PATENT DOCUMENTS

| | | |
|---|---|---|
| 2011/0293637 A1 | 12/2011 | Hacohen et al. |
| 2012/0059670 A1 | 3/2012 | Sanborn et al. |
| 2012/0066001 A1 | 3/2012 | Sanborn et al. |
| 2013/0124163 A1 | 5/2013 | Beckman |
| 2015/0252427 A1 | 9/2015 | Srivastava et al. |
| 2016/0101170 A1 | 4/2016 | Hacohen et al. |
| 2016/0339090 A1 | 11/2016 | Hacohen et al. |
| 2017/0028043 A1 | 2/2017 | Benz et al. |

FOREIGN PATENT DOCUMENTS

| | | |
|---|---|---|
| CN | 1833724 A | 9/2006 |
| CN | 103180730 A | 6/2013 |
| CN | 106456724 A | 2/2017 |
| CN | 108700592 A | 10/2018 |
| JP | 2018-535202 A | 11/2018 |
| KR | 10-2018-0087246 A | 8/2018 |
| MX | 2018004598 A | 11/2018 |
| MX | 2018004541 A | 4/2019 |
| WO | 2011/139345 A2 | 11/2011 |
| WO | 2013/062505 A1 | 5/2013 |
| WO | 2014/058987 A1 | 4/2014 |
| WO | 2014/082729 A1 | 6/2014 |
| WO | 2014/168874 A2 | 10/2014 |
| WO | 2015/049688 A2 | 4/2015 |
| WO | 2015095811 A2 | 6/2015 |
| WO | 2015/118529 A1 | 8/2015 |
| WO | 2015/164560 A1 | 10/2015 |
| WO | 2017/035392 A1 | 3/2017 |
| WO | 2017/066339 A1 | 4/2017 |

OTHER PUBLICATIONS

Carreno BM et al., "Cancer immunotherapy. A dendritic cell vaccine increases the breadth and diversity of melanoma neoantigen-specific T cells", Science, vol. 348, No. 6236, May 15, 2015, pp. 803-808, XP002772056, ISSN: 1095-9203, DOI: 10.1126/SCIENCE. AAA3828.
Mattos-Arruda et al., "Capturing intra-tumor genetic heterogeneity by de nova mutation profiling of circulating cell-free tumor DNA: a proof-of-principle", Annals of Oncology, Jul. 9, 2014, vol. 25, No. 9, pp. 1729-1735.
Tran et al., "Cancer Immunotherapy Based on Mutation-Specific CD4+ T Cells in a Patient with Epithelial Cancer", Science, May 9, 2014, vol. 344, No. 6184, pp. 641-645.
Tran E et al., "Supplementary Materials for Cancer Immunotherapy Based on Mutation-Specific CD4+ T Cells in a Patient with Epithelial Cancer", Science, May 9, 2014, vol. 344, No. 6184, pp. 29 pages.
Extended European Search Report dated May 17, 2019, for European Patent Application Serial No. 16856122.3, 13 pages.
Lundegaard et al., "NetMHC-3.0: accurate web accessible predictions of human, mouse and monkey MHC Class 1 affinities for peptides of length 8-11", Nucleic Acids Research, 2008, May 7, 2008,, vol. 36, pp. W509-W512.
Niazi et al., "Activation of human CD4 T cells by targeting MHC class II epitopes to endosomal compartments using human CD1 tail sequences", Immunology, May 21, 2007, vol. 122, pp. 522-531.
Duan et al., "Genomic and bioinformatics profiling of mutational neoepitopes reveals new rules to predict anticancer immunogenicity", The Journal of Experimental Medicine, Sep. 22, 2014, vol. 211, No. 11, pp. 2231-2248.
Zhang et al., "Dana-Farber Repository For Machine Learning In Immunology", J Immunol Methods, Nov. 30, 2011, vol. 374 , No. 1-2, pp. 18-25.
Amalfitano et al., "Production And Characterization Of Improved Adenovirus Vectors With The E1, E2b, And E3 Genes Deleted", Journal of Virology, Feb. 1998, vol. 72, No. 2, pp. 926-933.
Hosse et al., "A New Generation Of Protein Display Scaffolds For Molecular Recognition," Protein Science, 2006, vol. 15, pp. 14-27.
Carmen et al., "Concepts In Antibody Phage Display", Briefings In Functional Genomics And Proteomics, Jul. 2002, vol. 1, No. 2, pp. 189-203.
Dotti et al., "Design and Development of Therapies using Chimeric Antigen Receptor-Expressing T cells", Immunological Reviews, Jan. 2014, vol. 257, No. 1, p. 1-35.
Gubin et al., "Tumor Neoantigens: Building a Framework for Personalized Cancer Immunotherapy", The Journal of Clinical Investigation, Sep. 2015, vol. 125, No. 9, pp. 3413-3421.
International Search Report and Written Opinion received for PCT Application Serial No. PCT/US2016/056668 dated Mar. 27, 2017, 13 pages.
Charoentong et al., "Bioinformatics for cancer immunology and immunotherapy", Cancer Immunol Immunother, Sep. 18, 2012, vol. 61, pp. 1885-1903.
Non-Final Office Action received for U.S. Appl. No. 15/291,911 dated Jan. 26, 2017, 20 pages.
Final Office Action received for U.S. Appl. No. 15/291,911 dated Jun. 23, 2017, 28 pages.
Non-Final Office Action received for U.S. Appl. No. 15/291,911 dated Nov. 3, 2017, 19 pages.
Final Office Action received for U.S. Appl. No. 15/291,911 dated Dec. 5, 2018, 38 pages.
Non-Final Office Action received for U.S. Appl. No. 15/291,911 dated Apr. 30, 2019, 24 pages.
International Preliminary report on Patentability Chapter II received for PCT Application Serial No. PCT/US2016/056668 dated Jan. 31, 2018, 26 pages.
First Examination Report received for Australian Patent Application Serial No. 2016339022 dated Oct. 21, 2019, 04 pages.
Notice of Allowance received for U.S. Appl. No. 15/291,911 dated Sep. 16, 2019, 23 pages.
Notice of Reasons for Refusal received for Japaneses Application Serial No. 2018-519040, dated Jul. 28, 2020, 6 pages (incliding English Translation).
Communication pursuant to Article 94(3) EPC received for European Patent Application Serial No. 16856122.3 dated Jun. 25, 2021, 6 pages.
Second Office Action received for the Chinese Patent Application Serial No. 201680072233.X, dated Feb. 4, 2021, 9 pages (Including English Translation).
First Office Action received for the Chinese Application Serial No. 201680072233 X, dated Jun. 1, 2020, 17 pages (Including English Translation).
Dotti et al., "Design and development of therapies using chimeric antigen receptor-expressing T cells", Immunological Reviews, 2014, vol. 257, No. 1, pp. 107-126.
Notice of Allowance received for U.S. Appl. No. 15/291,911 dated Oct. 2, 2019, 23 pages.
Office Action received for Israeli Patent Application Serial No. IL258681 dated Aug. 24, 2021, 10 pages (Including English Translation).

(56) References Cited

OTHER PUBLICATIONS

Office Action received for Mexican Patent Application Serial No. MX/a/2018/004541 dated Nov. 11, 2020, 7 pages (Including English Translation).
Office Action received for Mexican Patent Application Serial No. MX/a/2018/004541 dated Jun. 17, 2021, 8 pages (Including English Translation).
Second Examination Report received for Australian Patent Application Serial No. 2016339022 dated Jun. 30, 2020, 6 pages.
Decision of Refusal received for Japanese Patent Application Serial No. 2018519040 dated May 11, 2021, 6 pages (Including English Translation).
Notice of Acceptance received for Australian Patent Application Serial No. 2016339022 dated Sep. 1, 2020, 03 pages.
Notification to Grant received for Chinese Patent Application Serial No. 201680072233.X dated Jul. 14, 2021, 3 pages.(including English Translation).
Office Action received for Canadian Patent Application Serial No. 3,003,305 dated Mar. 24, 2022, 7 pages.
Pre-Allowance Communication received for Israel Patent Application Serial No. 258681 dated May 26, 2022, 4 pages. (Including English Translation).
Pre-Allowance Notice received for Israel Patent Application Serial No. 258681 dated Sep. 28, 2022, 4 pages. (Including English Translation).
Office Action received for Canadian Patent Application Serial No. 3,003,305 dated Nov. 9, 2022, 6 pages.
Office Action received from Korean Patent Office dated Mar. 13, 2023 regarding Application Serial No. 101-2018-7013140 Application date May 9, 2018, 6 pages.

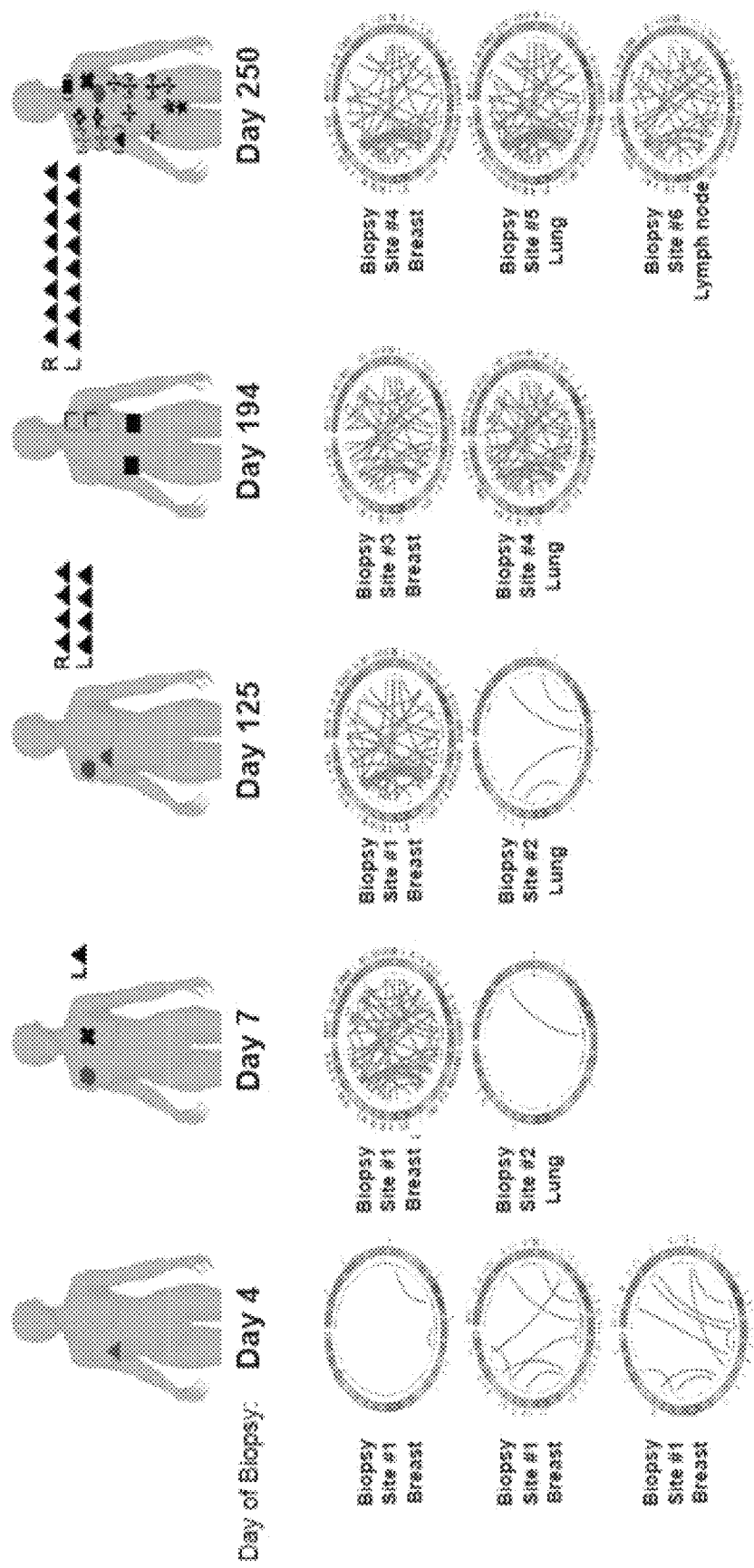

US 11,717,564 B2

ITERATIVE DISCOVERY OF NEOEPITOPES AND ADAPTIVE IMMUNOTHERAPY AND METHODS THEREFOR

This application is a continuation of allowed U.S. patent application Ser. No. 15/291,911, filed Oct. 12, 2016, claiming priority to U.S. provisional application with the Ser. No. 62/240,482, which was filed Oct. 12, 2015, and which is incorporated by reference herein.

FIELD OF THE INVENTION

The field of the invention is immunotherapeutic treatment of neoplastic diseases, and especially immunotherapeutic treatment of metastatic cancer.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Cancer treatment, and especially personalized cancer treatment has increasingly become a viable option for many patients. However, despite such improved treatments, recurrence is still often not successfully managed and may lead to less than desirable outcomes. Among other reasons, tumor heterogeneity (see e.g., WO 2015/164560) significantly reduces chances of proper choice of antigens that will lead to treatment success. Moreover, as is described in WO 2014/058987 many tumors develop clonally different metastases over time and may therefore not be targeted by immune treatment. Still further, treatment with other non-immunotherapeutic drugs will interfere in most cases with immunotherapeutic drug treatment.

Therefore, even though various cancer treatment options for immunotherapy are known in the art, there still remains a need for systems and methods that help improve treatment outcome in immunotherapy of cancer.

SUMMARY OF THE INVENTION

The inventors have discovered that recursive treatment of cancer that is guided by neoepitope analysis from various sites, and preferably different points in time, is significantly more likely to suppress or even eliminate recurrence of cancer. In especially preferred aspects, biopsies are taken from a patient's primary tumor, lymph nodes, and metastases, and each of these samples is subjected to omics analysis to obtain patient-, tumor-, and location-specific information of neoepitopes suitable for treatment with immunological compositions (e.g., antibodies, synbodies, modified NK cells, T-cells, recombinant viruses, etc.). The patient is then subjected to immunotherapy and optionally (low dose) chemotherapy, and subsequently further biopsies are taken from the same and/or new sites to monitor the presence, or increase or decrease of cancer cells harboring or displaying these epitopes as well as to identify new neoepitopes in these sites. Immunological and/or chemotherapeutic treatment is then adjusted to further treat the patient.

In one aspect of the inventive subject matter, the inventors contemplate a method of guided immunotherapy for a patient diagnosed with a tumor. In especially preferred methods, omics data are received for tumor cells in a first and second location in a patient, and the omics data are used to determine neoepitopes in the tumor cells of the first and second locations, respectively. In another step, treatment relevant neoepitopes are identified in the tumor cells of the first and second locations using at least one (or at least two, or at least three, or at least four) of a group attribute, a location attribute, a function attribute, a metabolic attribute, and/or a pathway attribute. An immunotherapeutic composition is created using the treatment relevant neoepitopes, and the immunotherapeutic composition is then administered to the patient.

While in certain aspects the patient may be treatment naïve, the patient may also have previously received treatment with an initial immunotherapeutic composition that may or may not be different from the created immunotherapeutic composition. Most typically, the first location will be a primary tumor while the second location may be a locoregional metastasis, a distant metastasis, a lymph node, or the circulatory system (e.g., where the tumor cell is a circulating tumor cell).

It is further generally preferred that the respective neoepitopes are determined by filtering against matched normal omics data and/or filtering against an HLA-type of the patient. With respect to the group attribute it is contemplated that such attribute may be a unique neoepitope, a shared neoepitope, and/or clonality status, that location attribute may be the primary tumor location, a metastasis location, and/or the circulatory system, and that the functional attribute may be a driver mutation or a passenger mutation. The metabolic attribute may be drug resistance or increased glycolysis, and the pathway attribute may be a mutation in a growth signaling pathway, a mutation in an apoptosis signaling pathway, a mutation in a hormonal signaling pathway, and/or a shift in signaling pathway usage.

Moreover, it is contemplated that suitable immunotherapeutic compositions include recombinant viral expression systems that encodes the treatment relevant neoepitopes, recombinant immune competent cells expressing the treatment relevant neoepitopes, recombinant immune competent cells expressing a receptor for the treatment relevant neoepitopes, synthetic antibodies for binding the treatment relevant neoepitopes, and white blood cells that were ex vivo activated with the treatment relevant neoepitopes. To continue targeting new neoepitopes, it is further contemplated that the steps of (a) receiving omics data for tumor cells in the first and second locations, (b) using the omics data to determine respective neoepitopes, (c) identifying treatment relevant neoepitopes, and (d) creating the immunotherapeutic composition using the treatment relevant neoepitopes may be repeated to thereby generate an updated immunotherapeutic composition.

Therefore, and viewed from a different perspective, the inventors also contemplate a method of optimizing immunotherapy for a patient having cancer that includes a step of receiving pre-treatment neoepitope sequence information for tumor cells in at least one of a first and a second location, and a further step of receiving post-treatment neoepitope sequence information for tumor cells in the at least one of the first and the second location. As noted above, each of the pre- and post-treatment neoepitope sequence information preferably has a group attribute, a location attribute, a function attribute, a metabolic attribute, and/or a pathway attribute. In yet another step, an updated treatment relevant neoepitope is identified based on the group attribute, the location attribute, the function attribute, the metabolic attribute, and/or the pathway attribute of the pre- and post-treatment neoepitope sequence information. An updated immunotherapeutic composition is then created using the updated treatment relevant neoepitopes, and the updated immunotherapeutic composition is administered to the patient.

Most typically, the first location is a primary tumor and the second location is a locoregional metastasis, a distant metastasis, a lymph node, or the circulatory system. For example, the pre- and post-neoepitope sequence information are from tumor cells in the first and second locations, and the updated treatment relevant neoepitope may be based on at least two of the group attribute, the location attribute, and the function attribute of the pre- and post-treatment neoepitope sequence information. As noted above it is generally preferred that the group attribute may be a unique neoepitope, a shared neoepitope, or clonality status, the location attribute may be a primary tumor location, a metastasis location, or a circulatory system, and the functional attribute may be a driver mutation, a passenger mutation, a mutation in a growth signaling pathway, a mutation in an apoptosis signaling pathway, or a mutation in a hormonal signaling pathway. Likewise, it is generally preferred that the immunotherapeutic composition may be a recombinant viral expression system that encodes the treatment relevant neoepitopes, a recombinant immune competent cell expressing the treatment relevant neoepitopes, a recombinant immune competent cell expressing a receptor for the treatment relevant neoepitopes, a synthetic antibody for binding the treatment relevant neoepitopes, or a population of white blood cells ex vivo activated with the treatment relevant neoepitopes.

Consequently, the inventors also contemplate a method of improving treatment for a patient diagnosed with a tumor. Preferred methods include a step of receiving a plurality of first omics data for tumor cells of a patient, wherein the first omics data are obtained from at least two different locations of the tumor cells. In a further step, patient-, cancer-, and location-specific neoepitopes are determined from the first omics data, each having at least one of a group attribute, a location attribute, a function attribute, a metabolic attribute, and/or a pathway attribute, and the neoepitopes are subsequently used to generate a patient-specific immunotherapeutic composition. In a still further step, a plurality of second omics data is received for tumor cells of the patient, wherein the second omics data are obtained from at least two different locations of the tumor cells, and wherein the second omics data are obtained after treatment of the patient with the patient-specific immunotherapeutic composition. Once more, updated patient-, cancer-, and location-specific neoepitopes are determined from the second omics data, each having at least one of a group attribute, a location attribute, a function attribute, a metabolic attribute, and/or a pathway attribute, and the updated neoepitopes are used to generate an updated patient-specific immunotherapeutic composition.

With respect to the first and second locations, the attributes, and the patient-specific immunotherapeutic composition, the same considerations as provided above apply. In addition, it is generally contemplated that the patient-specific immunotherapeutic composition and the updated patient-specific immunotherapeutic composition are different entities selected from the group consisting of a recombinant viral expression system that encodes the treatment relevant neoepitopes, a recombinant immune competent cell expressing the treatment relevant neoepitopes, a recombinant immune competent cell expressing a receptor for the treatment relevant neoepitopes, a synthetic antibody for binding the treatment relevant neoepitopes, and a population of white blood cells ex vivo activated with the treatment relevant neoepitopes.

Various objects, features, aspects and advantages of the inventive subject matter will become more apparent from the following detailed description of preferred embodiments, along with the accompanying drawing FIGURES in which like numerals represent like components.

BRIEF DESCRIPTION OF THE DRAWING

FIG. 1 is an exemplary illustration of tumor heterogeneity across different locations and points in time.

DETAILED DESCRIPTION

The inventors have discovered that treatment of various cancers can be significantly improved using recursive identification of patient-, tumor-, and location-specific neoepitopes after immunotherapy and/or chemotherapy and that such subsequently identified neoepitopes can be used as new therapeutic targets to refine or adjust immunotherapy. Most notably, such approach also allows targeting specific subpopulations of tumors and/or metastases that may otherwise not be treated using conventional treatment. Moreover, contemplated systems and methods will allow updating of treatment targets even where tumors are subject to high rates of genetic changes.

In this context, it should be appreciated that preferred neoepitopes are not epitopes that are common to cancers (e.g., CEA) or epitopes that are specific to a particular type of cancer (e.g., PSA), but antigens that are exclusive to the particular tumor or even location within the tumor. Moreover, it should be appreciated that preferred neoepitopes are also specific to the particular patient (thus eliminating SNPs and other known variants) and his or her HLA-type as is discussed in more detail below. Lastly, as is also discussed in more detail below, neoepitopes suitable for use herein are specific with respect to their anatomical location. Viewed from a different perspective, contemplated neoepitopes are genuine to the specific patient and his/her HLA-type, the tumor, and the location. In addition, neoepitopes may further be specific to a particular treatment phase (e.g., prior to treatment, subsequent to a first round of treatment, etc.).

In contrast, where neoepitopes are determined from a tumor sample using a standard 'healthy' reference sequence, a large number of such neoepitopes are likely false positives due to idiosyncratic SNPs. Moreover, where the patient's HLA type is not taken into account, a significant number of neoepitopes will not be 'visible' to the immune system, even if the neoepitope is a patient-specific neoepitope. Thus, most currently known neoepitope systems and methods will provide a significant quantity of false-positive results that may result in no therapeutic effect. Moreover, where neoepitope analysis is based only on a single sample, the genetic heterogeneity of tumors over anatomical location and time will render most immune treatments ineffective or less effective. FIG. 1 exemplarily illustrates the challenge to immunotherapy. Here, a patient diagnosed with triple negative breast cancer was subjected to multiple biopsies at different times and locations as indicated. In addition, the patient also received treatment with cisplatin starting at day 7 and with veliparib starting on day 125. As can be seen from the circle plots for each biopsy and point in time, the tumors and metastases were genetically diverse and dynamic. In view of this heterogeneity, immunotherapy using a single neoepitope without further analysis of other neoepitopes across various locations and time is unlikely to result in a desired therapeutic outcome. To overcome this challenge, the inventors now contemplate method of guided immunotherapy for a patient diagnosed with a tumor that includes the steps of (a) receiving omics data for tumor cells in a first location in a patient, and receiving omics data for tumor cells in a second location in a patient; (b) using the omics data to determine respective neoepitopes in the tumor cells of the first and second locations; (c) identifying treatment relevant neoepitopes in the tumor cells of the first and second locations using at least one of a group attribute, a location attribute, and a function attribute; (d) and creating an immunotherapeutic composition using the treatment relevant neoepitopes, and administering the immunotherapeutic composition to the patient.

Viewed from another perspective, the inventors therefore also contemplate a method of optimizing immunotherapy for a patient having cancer that includes the steps of (a) receiving pre-treatment neoepitope sequence information for tumor cells in at least one of a first and a second location; (b) receiving post-treatment neoepitope sequence information for tumor cells in the at least one of the first and the second location; (c) wherein each of the pre- and post-treatment neoepitope sequence information has a group attribute, a location attribute, and a function attribute; (d) identifying an updated treatment relevant neoepitope based on at least one of the group attribute, the location attribute, and the function attribute of the pre- and post-treatment neoepitope sequence information; and (e) creating an updated immunotherapeutic composition using the updated treatment relevant neoepitopes, and administering the updated immunotherapeutic composition to the patient.

Therefore, and viewed from yet another perspective, the inventors also contemplate a method of improving treatment for a patient diagnosed with a tumor that includes the steps of (a) receiving a plurality of first omics data for tumor cells of a patient, wherein the first omics data are obtained from at least two different locations of the tumor cells; (b) determining patient-, cancer-, and location-specific neoepitopes from the first omics data, each having at least one of a group attribute, a location attribute, and a function attribute; (c) using the neoepitopes to generate a patient-specific immunotherapeutic composition; (d) receiving a plurality of second omics data for tumor cells of the patient, wherein the second omics data are obtained from at least two different locations of the tumor cells, and wherein the second omics data are obtained after treatment of the patient with the patient-specific immuno-therapeutic composition; (e) determining updated patient-, cancer-, and location-specific neoepitopes from the second omics data, each having at least one of a group attribute, a location attribute, and a function attribute; and (f) using the updated neoepitopes to generate an updated patient-specific immunotherapeutic composition.

With respect to neoepitopes, it should be appreciated that neoepitopes can be viewed as expressed random mutations in tumor cells that created unique and tumor specific antigens. Therefore, viewed from a different perspective, neoepitopes may be identified by considering the type (e.g., deletion, insertion, transversion, transition, translocation) and impact of the mutation (e.g., non-sense, missense, frame shift, etc.), which may as such serve as a first content filter through which silent and other non-relevant (e.g., non-expressed) mutations are eliminated. It should further be appreciated that neoepitope sequences can be defined as sequence stretches with relatively short length (e.g., 7-11 mers) wherein such stretches will include the change(s) in the amino acid sequences. Most typically, the changed amino acid will be at or near the central amino acid position. For example, a typical neoepitope may have the structure of $A_4$-N-$A_4$, or $A_3$-N-$A_5$, or $A_2$-N-$A_7$, or $A_5$-N-$A_3$, or $A_7$-N-$A_2$, where A is a proteinogenic amino acid and N is a changed amino acid (relative to wild type or relative to matched normal). For example, neoepitope sequences as contemplated herein include sequence stretches with relatively short length (e.g., 5-30 mers, more typically 7-11 mers, or 12-25 mers) wherein such stretches include the change(s) in the amino acid sequences.

Thus, it should be appreciated that a single amino acid change may be presented in numerous neoepitope sequences that include the changed amino acid, depending on the position of the changed amino acid. Advantageously, such sequence variability allows for multiple choices of neoepitopes and so increases the number of potentially useful targets that can then be selected on the basis of one or more desirable traits (e.g., highest affinity to a patient HLA-type, highest structural stability, etc.). Most typically, such neoepitopes will be calculated to have a length of between 2-50 amino acids, more typically between 5-30 amino acids, and most typically between 9-15 amino acids, with a changed amino acid preferably centrally located or otherwise situated in a manner that allows for or improves its binding to MEW. For example, where the epitope is to be presented by the MHC-I complex, a typical neoepitope length will be about 8-11 amino acids, while the typical neoepitope length for presentation via MHC-II complex will have a length of about 13-17 amino acids. As will be readily appreciated, since the position of the changed amino acid in the neoepitope may be other than central, the actual peptide sequence and with that actual topology of the neoepitope may vary considerably.

Of course, it should be appreciated that the identification or discovery of neoepitopes may start with a variety of biological materials, including fresh biopsies, frozen or otherwise preserved tissue or cell samples, circulating tumor cells, exosomes, various body fluids (and especially blood), etc. as is further discussed in more detail below. Thus, suitable methods of omics analysis include nucleic acid sequencing, and particularly NGS methods operating on DNA (e.g., Illumina sequencing, ion torrent sequencing, 454 pyrosequencing, nanopore sequencing, etc.), RNA sequencing (e.g., RNAseq, reverse transcription based sequencing, etc.), and protein sequencing or mass spectroscopy based sequencing (e.g., SRM, MRM, CRM, etc.).

As such, and particularly for nucleic acid based sequencing, it should be particularly recognized that high-throughput genome sequencing of a tumor tissue will allow for rapid identification of neoepitopes. However, it must be appreciated that where the so obtained sequence information is compared against a standard reference, the normally occurring inter-patient variation (e.g., due to SNPs, short indels, different number of repeats, etc.) as well as heterozygosity will result in a relatively large number of potential false positive neoepitopes. Notably, such inaccuracies can be eliminated where a tumor sample of a patient is compared against a matched normal (i.e., non-tumor) sample of the same patient.

In one especially preferred aspect of the inventive subject matter, DNA analysis is performed by whole genome sequencing and/or exome sequencing (typically at a coverage depth of at least 10×, more typically at least 20×) of both tumor and matched normal sample. Alternatively, DNA data may also be provided from an already established sequence record (e.g., SAM, BAM, FASTA, FASTQ, or VCF file) from a prior sequence determination. Therefore, data sets may include unprocessed or processed data sets, and exemplary data sets include those having BAMBAM format, SAMBAM format, FASTQ format, or FASTA format. However, it is especially preferred that the data sets are provided in BAMBAM format or as BAMBAM diff objects (see e.g., US2012/0059670A1 and US2012/0066001A1). Moreover, it should be noted that the data sets are reflective of a tumor and a matched normal sample of the same patient to so obtain patient and tumor specific information. Thus, genetic germ line alterations not giving rise to the tumor (e.g., silent mutation, SNP, etc.) can be excluded. Of course, and addressed in more detail below, it should be recognized that the tumor sample may be from an initial tumor, from the tumor upon start of treatment, from a recurrent tumor or metastatic site, etc. In most cases, the matched normal sample of the patient may be blood, or non-diseased tissue from the same tissue type as the tumor.

Of course, it should be noted that the computational analysis of the sequence data may be performed in numerous manners. In most preferred methods, however, analysis is performed in silico by location-guided synchronous alignment of tumor and normal samples as, for example, disclosed in US 2012/0059670A1 and US 2012/0066001A1 using BAM files and BAM servers. Such analysis advantageously reduces false positive neoepitopes and significantly reduces demands on memory and computational resources.

Additionally, it should be appreciated that the analysis may also be performed in a manner where the matched normal sequence data are replaced with tumor sequence data from a different point in time and/or a different location. Thus, analysis of a tumor may not only be performed in a manner that compared tumor sequence information with matched normal sequence information, but also in a manner that allows detection of differential mutations in a tumor at one location over time (e.g., primary tumor before and after first round of treatment) or in a primary tumor versus other location (e.g., primary tumor versus distant metastasis). Thus, genetic drift and with that neoepitope drift can be identified and treatment can be readily adapted. Moreover, the effect of a prior round of treatment can be correlated with the presence or absence of neoepitopes, which may be used as molecular proxy markers for efficacy of treatment. For example, immunotherapy using a first neoepitope may result in the eradication of a tumor cell population or clone expressing that neoepitope while treatment resistant claims with new neoepitopes may be readily identified and followed. Viewed from a different perspective, differential neoepitope analysis from biopsy data of the same patient may not only be useful for generation of a new immunotherapeutic, but also for tracking and evaluation of prior treatment.

It should be noted that any language directed to a computer should be read to include any suitable combination of computing devices, including servers, interfaces, systems, databases, agents, peers, engines, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclosed apparatus. Further, the disclosed technologies can be embodied as a computer program product that includes a non-transitory computer readable medium storing the software instructions that causes a processor to execute the disclosed steps associated with implementations of computer-based algorithms, processes, methods, or other instructions. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges among devices can be conducted over a packet-switched network, the Internet, LAN, WAN, VPN, or other type of packet switched network; a circuit switched network; cell switched network; or other type of network.

Viewed from a different perspective, a patient-, cancer-, and location-specific in silico collection of sequences can be established that have a predetermined length of between 5 and 25 amino acids and include at least one changed amino acid. Such collection will typically include for each changed amino acid at least two, at least three, at least four, at least five, or at least six members in which the position of the changed amino acid is not identical. Such collection can then be used for further filtering (e.g., by sub-cellular location, transcription and/or expression level, MHC-I and/or II affinity, etc.) as is described in more detail below.

Depending on the type and stage of the cancer, it was observed that only a fraction of neoepitopes will generate an immune response. To increase likelihood of a therapeutically effective response, the neoepitopes can be further filtered. Of course, it should be appreciated that downstream analysis need not take into account silent mutations for the purpose of the methods presented herein. However, preferred mutation analyses will provide in addition to the type of mutation (e.g., deletion, insertion, transversion, transition, translocation) also information of the impact of the mutation (e.g., non-sense, missense, etc.) and may as such serve as a first content filter through which silent mutations are eliminated. For example, neoepitopes can be selected for further consideration where the mutation is a frame-shift, non-sense, and/or missense mutation. Such filtering may be performed using sequencing data or in silico translated sequences.

In a further filtering approach, neoepitopes may also be subject to detailed analysis for sub-cellular location parameters. For example, neoepitope sequences may be selected for further consideration if the neoepitopes are identified as having a membrane associated location (e.g., are located at the outside of a cell membrane of a cell) and/or if an in silico structural calculation confirms that the neoepitope is likely to be solvent exposed, or presents a structurally stable epitope (e.g., *J Exp Med* 2014), etc.

With respect to filtering neoepitopes, it is generally contemplated that neoepitopes are especially suitable for use herein where omics (or other) analysis reveals that the neoepitope is actually expressed. Identification of expression and expression level of a neoepitope can be performed in all manners known in the art and preferred methods include quantitative RNA (hnRNA or mRNA) analysis and/or quantitative proteomics analysis. Most typically, the threshold level for inclusion of neoepitopes will be an expression level of at least 20%, at least 30%, at least 40%, or at least 50% of expression level of the corresponding matched normal sequence, thus ensuring that the (neo) epitope is at least potentially 'visible' to the immune system.

Consequently, it is generally preferred that the omics analysis also includes an analysis of gene expression (transcriptomic analysis) to so help identify the level of expression for the gene with a mutation.

There are numerous methods of transcriptomic analysis known in the art, and all of the known methods are deemed suitable for use herein. For example, preferred materials include mRNA and primary transcripts (hnRNA), and RNA sequence information may be obtained from reverse transcribed polyA$^+$-RNA, which is in turn obtained from a tumor sample and a matched normal (healthy) sample of the same patient. Likewise, it should be noted that while polyA$^+$-RNA is typically preferred as a representation of the transcriptome, other forms of RNA (hnRNA, non-polyadenylated RNA, siRNA, miRNA, etc.) are also deemed suitable for use herein. Preferred methods include quantitative RNA (hnRNA or mRNA) analysis and/or quantitative proteomics analysis, especially including RNAseq. In other aspects, RNA quantification and sequencing is performed using RNA-seq, qPCR and/or rtPCR based methods, although various alternative methods (e.g., solid phase hybridization-based methods) are also deemed suitable. Viewed from another perspective, transcriptomic analysis may be suitable (alone or in combination with genomic analysis) to identify and quantify genes having a cancer- and patient-specific mutation.

Similarly, proteomics analysis can be performed in numerous manners to ascertain actual translation of the RNA of the neoepitope, and all known manners of proteomics analysis are contemplated herein. However, particularly preferred proteomics methods include antibody-based methods and mass spectroscopic methods. Moreover, it should be noted that the proteomics analysis may not only provide qualitative or quantitative information about the protein per se, but may also include protein activity data where the protein has catalytic or other functional activity. One exemplary technique for conducting proteomic assays is described in U.S. Pat. No. 7,473,532, incorporated by reference herein. Further suitable methods of identification and even quantification of protein expression include various mass spectroscopic analyses (e.g., selective reaction monitoring (SRM), multiple reaction monitoring (MRM), and consecutive reaction monitoring (CRM)).

In yet another aspect of filtering, the neoepitopes may be compared against a database that contains known human sequences (e.g., of the patient or a collection of patients) to so avoid use of a human-identical sequence. Moreover, filtering may also include removal of neoepitope sequences that are due to SNPs in the patient where the SNPs are present in both the tumor and the matched normal sequence. For example, dbSNP (The Single Nucleotide Polymorphism Database) is a free public archive for genetic variation within and across different species developed and hosted by the National Center for Biotechnology Information (NCBI) in collaboration with the National Human Genome Research Institute (NHGRI). Although the name of the database implies a collection of one class of polymorphisms only (single nucleotide polymorphisms (SNPs)), it in fact contains a relatively wide range of molecular variation: (1) SNPs, (2) short deletion and insertion polymorphisms (indels/DIPs), (3) microsatellite markers or short tandem repeats (STRs), (4) multinucleotide polymorphisms (MNPs), (5) heterozygous sequences, and (6) named variants. The dbSNP accepts apparently neutral polymorphisms, polymorphisms corresponding to known phenotypes, and regions of no variation.

Using such database and other filtering options as described above, the patient and tumor specific neoepitopes may be filtered to remove those known sequences, yielding a sequence set with a plurality of neoepitope sequences having substantially reduced false positives.

Nevertheless, despite filtering, it should be recognized that not all neoepitopes will be visible to the immune system as the neoepitopes also need to be presented on the MHC complex of the patient. Indeed, only a fraction of the neoepitopes will have sufficient affinity for presentation, and the large diversity of MHC complexes will preclude use of most, if not all, common neoepitopes. Therefore, in the context of immune therapy it should be readily apparent that neoepitopes will be more likely effective where the neoepitopes are bound to and presented by the MHC complexes. Viewed from a different perspective, it should be appreciated that effective binding and presentation is a combined function of the sequence of the neoepitope and the particular HLA-type of a patient. Most typically, suitable HLA-type determinations include at least three MHC-I sub-types (e.g., HLA-A, HLA-B, HLA-C) and at least one, or two, or three MHC-II sub-types (e.g., HLA-DP, HLA-DQ, HLA-DR). Preferably each subtype will be determined to at least 4-digit depth. However, greater depth (e.g., 6 digit, 8 digit) is also contemplated herein.

HLA determination can be performed using various methods in wet-chemistry that are well known in the art, and all of these methods are deemed suitable for use herein. Once the HLA-type of the patient is ascertained (using known chemistry or in silico determination), a structural solution for the HLA-type can be calculated or obtained from a database, which is then used in a docking model in silico to determine binding affinity of the (typically filtered) neoepitope to the HLA structural solution. As will be further discussed below, suitable systems for determination of binding affinities include the NetMHC platform (see e.g., *Nucleic Acids Res.* 2008 Jul. 1; 36(Web Server issue): W509-W512.). Neoepitopes with high affinity (e.g., less than 100 nM, less than 75 nM, less than 50 nM) for a previously determined HLA-type are then selected for therapy creation, along with the knowledge of the patient's MHC-I/II subtype.

In especially preferred methods, the HLA-type can be predicted from the patient's omics data in silico using a reference sequence containing most or all of the known and/or common HLA-types. For example, in one exemplary method, a relatively large number of patient sequence reads mapping to chromosome 6p21.3 (or any other location near/at which HLA alleles are found) is provided by a database or sequencing machine. Most typically the sequence reads will have a length of about 100-300 bases and comprise metadata, including read quality, alignment information, orientation, location, etc. For example, suitable formats include SAM, BAM, FASTA, GAR, etc. While not limiting to the inventive subject matter, it is generally preferred that the patient sequence reads provide a depth of coverage of at least 5×, more typically at least 10×, even more typically at least 20×, and most typically at least 30×.

In addition to the patient sequence reads, contemplated methods further employ one or more reference sequences that include a plurality of sequences of known and distinct HLA alleles. For example, a typical reference sequence may be a synthetic (without corresponding human or other mammalian counterpart) sequence that includes sequence segments of at least one HLA-type with multiple HLA-alleles of that HLA-type. For example, suitable reference sequences include a collection of known genomic sequences for at least 50 different alleles of HLA-A. Alternatively, or additionally, the reference sequence may also include a collection of known RNA sequences for at least 50 different alleles of HLA-A. Of course, the reference sequence is not limited to 50 alleles of HLA-A, but may have alternative composition with respect to HLA-type and number/composition of alleles. Most typically, the reference sequence will be in a computer readable format and will be provided from a database or other data storage device. For example, suitable reference sequence formats include FASTA, FASTQ, EMBL, GCG, or GenBank format, and may be directly obtained or built from data of a public data repository (e.g., IMGT, the International ImMunoGeneTics information system, or The Allele Frequency Net Database, EUROSTAM). Alternatively, the reference sequence may also be built from individual known HLA-alleles based on one or more predetermined criteria such as allele frequency, ethnic allele distribution, common or rare allele types, etc.

Using the reference sequence, the patient sequence reads can now be threaded through a de Bruijn graph to identify the alleles with the best fit. In this context, it should be noted that each individual carries two alleles for each HLA-type, and that these alleles may be very similar, or in some cases even identical. Such high degree of similarity poses a significant problem for traditional alignment schemes. The inventor has now discovered that the HLA alleles, and even very closely related alleles can be resolved using an approach in which the de Bruijn graph is constructed by decomposing a sequence read into relatively small k-mers (typically having a length of between 10-20 bases), and by implementing a weighted vote process in which each patient sequence read provides a vote ("quantitative read support") for each of the alleles on the basis of k-mers of that sequence read that match the sequence of the allele. The cumulatively highest vote for an allele then indicates the most likely predicted HLA allele. In addition, it is generally preferred that each fragment that is a match to the allele is also used to calculate the overall coverage and depth of coverage for that allele.

Scoring may further be improved or refined as needed, especially where many of the top hits are similar (e.g., where a significant portion of their score comes from a highly shared set of k-mers). For example, score refinement may include a weighting scheme in which alleles that are substantially similar (e.g., >99%, or other predetermined value) to the current top hit are removed from future consideration. Counts for k-mers used by the current top hit are then re-weighted by a factor (e.g., 0.5), and the scores for each HLA allele are recalculated by summing these weighted counts. This selection process is repeated to find a new top hit. The accuracy of the method can be even further improved using RNA sequence data that allows identification of the alleles expressed by a tumor, which may sometimes be just 1 of the 2 alleles present in the DNA. In further advantageous aspects of contemplated systems and methods, DNA or RNA, or a combination of both DNA and RNA can be processed to make HLA predictions that are highly accurate and can be derived from tumor or blood DNA or RNA. Further aspects, suitable methods and considerations for high-accuracy in silico HLA typing are described in International PCT/US16/48768, incorporated by reference herein.

Once patient/tumor specific neoepitopes and HLA-type are identified, computational analysis can be performed by docking neoepitopes to the HLA and determining best binders (e.g., lowest $K_D$, for example, less than 500 nM, or less than 250 nM, or less than 150 nM, or less than 50 nM), for example, using NetMHC. It should be appreciated that such approach will not only identify specific neoepitopes that are genuine to the patient and tumor for each location, but also those neoepitopes that are most likely to be presented on a cell and as such most likely to elicit an immune response with therapeutic effect. Of course, it should also be appreciated that thusly identified HLA-matched neoepitopes can be biochemically validated in vitro (e.g., to establish high-affinity binding between MEW complex and neoepitope and/or presentation) prior to use in a therapeutic composition.

Of course, it should be appreciated that matching of the patient's HLA-type to the patient- and cancer-specific neoepitope can be done using systems other than NetMHC, and suitable systems include NetMHC II, NetMHCpan, IEDB Analysis Resource, RankPep, PREDEP, SVMHC, Epipredict, HLABinding, and others (see e.g., *J Immunol Methods* 2011; 374:1-4). In calculating the highest affinity, it should be noted that the collection of neoepitope sequences in which the position of the altered amino acid is moved (supra) can be used. Alternatively, or additionally, modifications to the neoepitopes may be implemented by adding N- and/or C-terminal modifications to further increase binding of the expressed neoepitope to the patient's HLA-type. Thus, neoepitopes may be native as identified or further modified to better match a particular HLA-type. Moreover, where desired, binding of corresponding wild type sequences (i.e., neoepitope sequence without amino acid change) can be calculated to ensure high differential affinities. For example, especially preferred high differential affinities in MEW binding between the neoepitope and its corresponding wild type sequence are at least 2-fold, at least 5-fold, at least 10-fold, at least 100-fold, at least 500-fold, at least 1000-fold, etc.).

In especially contemplated aspect of the inventive subject matter, to identify treatment relevant neoepitopes in the tumor cells, several biopsies are taken from at least two and more typically at least three locations in a patient diagnosed with cancer. Most typically, such biopsies will include a biopsy from the primary tumor, from a lymph node proximal to the tumor, one or more locoregional metastases, and one or more distant metastases, typically within a relatively narrow time frame (e.g., same day). Of course, it should be appreciated that all manners of biopsies are deemed suitable and include fresh (liquid and solid) biopsies, flash-frozen biopsies, FFPE samples, etc. These distinct biopsies are then subjected to omics analysis to obtain respective omics data for each of the sites, which are then used to design a patient-, disease-, and location-specific immunotherapy or chemotherapy using treatment relevant neoepitopes.

It should be noted that multiple biopsies and associated multiple neoepitopes will advantageously provide not only a more representative picture of mutational changes across all occurrences of cancerous tissue, but also allows for treatment surveillance and adaptation over time. Still further, and depending on the particular manner of attribution as described below, treatment may be tailored towards one or more particular aspects or subclones (e.g., targeting only metastatic cells, or targeting only chemotherapy resistant cells, or targeting founder mutations, etc.). As multiple biopsies are present, and as the number of potential targets for therapy increases, the neoepitopes identified as described above are further subject to attribution to reduce the possible number of permutations to a clinically relevant set of neoepitopes to achieve a particular purpose.

Most preferably, attribution will include at least one (or at least two, or at least three, or at least four) of a group attribute, a location attribute, a function attribute, a metabolic attribute, a pathway attribute. For example, where the attribute is a group attribute, the group attribute will provide information about the neoepitope vis-à-vis other neoepitopes of the same patient. Suitable group attributes will therefore include identification of the neoepitope as being a unique neoepitope, or as being a shared neoepitope (e.g., shared between the primary tumor and a tumor cell in a draining lymph node, or shared among all tumor cells in all biopsies), identification of the ploidy status (e.g., aneuploid, polyploidy, etc.), clonality status (e.g., belonging to a specific subclone within a group of subclones), time of detection by a diagnostic test (e.g., present at first diagnosis, later-developed tumor or metastasis), and/or the type of the diseased tissue in which the neoepitope is found (e.g., primary tumor, metastasis, etc.), etc. With respect to the clonality analysis it is preferred that the analysis is performed on the basis of existing omics data, and especially suitable clonality analysis is performed using methods as taught in WO 2014/058987. Of course, it should be appreciated that each specific group attribute may comprise more than one descriptor.

Suitable location attributes will generally provide descriptive information as to the gross and fine anatomical location of the neoepitope. For example, location attributes will include tumor location (e.g., by organ and/or affected cellular structure(s)), location of the metastasis (e.g., lymph node, locoregional, distant), and information whether or not the neoepitope is found in cells in the circulatory system or bone marrow (e.g., circulating tumor cells). With respect to the functional attribute, it is contemplated that the functional attribute will provide information as to the functional impact that the neoepitope has or is suspected to have. For example, functional attributes will include identification of the neoepitope as being (or associated with) a driver mutation or a passenger mutation. Other examples of functional attributes also include methylation status or splice variant of the nucleic acid encoding the neoepitope.

In still further contemplated aspects of the inventive subject matter, the neoepitope may also have a metabolic attribute that provides metabolic information about the cells with which the neoepitope is associated. For example, a neoepitope may be found in a population of cells that are resistant to a particular drug, or that are sensitive to a drug or treatment type. Metabolic information may also include respiratory status of the cell (e.g., increased lactic acid levels or activity of glycolytic enzymes), presence or absence of nutrient transporters on the cell surface (e.g., glucose transporter GLUT1, the amino acid transporter dimerization partner 4F2hc, net amino acid transporters like EAT2, SNAT1/2, etc.). Likewise, the nature of the pathway attribute may also vary considerably and will generally include pathway information of the cell in which the neoepitope is observed (e.g., regarding functional impact of a mutation or one or more defects or changes in pathway activity). For example, suitable pathway attributes include information about mutation in or function of a growth signaling pathway, mutation in or function of an apoptosis signaling pathway, mutation in or function of a hormonal signaling pathway, and/or a shift in a signaling pathway usage. Notably, such pathway information may be obtained from the same omics data, and pathway analysis may reveal increased or decreased activity of a signaling protein, or a constitutively active receptor protein or domain. There are various manners of pathway analysis known in the art, and all of them are deemed appropriate for use herein. However, in especially preferred aspects, pathway analysis is performed using PARADIGM (see e.g., as described in WO 2011/139345 or WO 2013/062505).

Upon determination of neoepitopes and associated attributes, it should be appreciated that the so obtained information is not merely a collection of sequences that may be useful for generation of an immunotherapeutic agent, but that the identified sequences provide genetic, physiologic, and temporal 'metadata' that can guide proper target selection for an improved immunotherapeutic treatment composition. For example, where primary and metastatic tumors have the same neoepitope that is associated with a driver mutation, that neoepitope may be particularly suitable as a target using immunotherapy to eradicate all neoplastic growth. On the other hand, where two metastases of a primary tumor share a common neoepitope, immunotherapy targeting the common neoepitope may be implemented while the primary tumor can be surgically removed. Thus, and viewed form a different perspective, neoepitope sequences may be selected on the basis of at least one, or at least two, or at least three, or least four attributes to target a specific tumor clone, a specific location, or all of the tumor growth.

For example, group attributes may be used to identify individual neoepitopes that may be useful for comprehensive therapy (e.g., where the group attribute is a shared neoepitope) to eliminate cancer from the patient, or for a highly targeted therapy (e.g., where the group attribute is a unique neoepitope) where the tumor in the patient is in an inoperable location or fast removal is otherwise required. On the other hand, where the group attribute identifies the ploidy status, the group attribute may be used to preferentially target cells with an amplified (overactive) signaling component. On the other hand, where the group attribute is clonality status, the attribute may be used to target a fast-growing or highly metastatic subclone. In still further examples, where the group attribute is time of detection by a diagnostic test or type of the diseased tissue, later-developed tumors or metastases may be targeted first while the primary tumor may be treated using chemotherapy.

With respect to location attributes it should be recognized that neoepitopes may be identified that are specific for the gross/or fine anatomical location of the neoepitope. As such, tumors and/or metastases may be selectively treated to avoid surgical removal where such removal may not be feasible or be too risky (e.g., brain or liver metastases). Likewise, functional attributes may be especially useful where the neoepitope is in or associated with a driver mutation. In such case, tumor growth and progression may be effectively halted or slowed down where such neoepitope is targeted by immunotherapy. On the other hand, drug treatment rather than immunotherapy may be advised where the attribute is a metabolic attribute indicating that the tumor cell is sensitive to a drug or other treatment modality. Likewise, where a pathway attribute indicates a constitutively active receptor, drug treatment may be implemented to stop or reduce signal flow through that signaling pathway.

Of course, it should be recognized that information from the different attributes may be combined to further define treatment options and targets. For example, group attributes and location attributes may be used to identify one or more common targets for treatment with an immunotherapeutic agent, while metabolic attributes may be employed to identify remaining tumors that may be sensitive to non-immunotherapeutic drugs. Viewed from a different perspective, it should be appreciated that various mathematical operations using operations from set theory may be employed on various attributes to select specific neoepitopes in a purposive manner. For example, contemplated operations for use in conjunction with the teachings herein include union, intersection, power set, set difference, symmetric difference, and Cartesian product. All of such operations will result in one or more neoepitopes that are targeted to one or more specific treatment outcomes.

Thus, analysis may also reveal that immunotherapy treatment may be suitable for one subset of tumors while other tumors could be treated in the same patient in more conventional manners, including radiation, chemotherapy, and/ or radiation therapy. Likewise, the methods presented herein may reveal that immunotherapy may be augmented with other therapeutic modalities, including radiation, chemotherapy, and/or radiation therapy. Still further, it should also be noted that one or more attributes may even be used in non-immunotherapeutic treatment to follow or quantify treatment progress. For example, disappearance of unique neoepitopes of the primary tumor may be used as a proxy marker of drug treatment targeting the primary tumor (e.g., using angiogenesis inhibitors), while disappearance of shared neoepitopes among circulating tumor cells may be used to follow or quantify treatment effect of immune checkpoint inhibitors. Similarly, emergence of new neoepitopes following a round of treatment may be used to identify genetic drift of the remaining tumor cells, which can be used in subsequent design of immunotherapeutic agents.

Regardless of the particular use of the neoepitope attributes, it should be appreciated that the so identified and selected neoepitope or neoepitopes may be used in the creation of an immunotherapeutic composition for the particular patient. Thus, it should be noted that the methods presented herein will advantageously allow for the direct or indirect creation of an HLA matched patient-, tumor-, and location-specific immunotherapeutic composition. As used herein, the terms "creating" or "creation" in the context of an immunotherapeutic composition is meant to also include causing to create the immunotherapeutic composition. For example, an immunotherapeutic composition may be directly created by producing a vaccine, an antibody or other neoepitope-specific affinity reagent, or a neoepitope-specific cell based composition, or indirectly, by providing information about selected neoepitopes to a manufacturer that generates the immunotherapeutic composition.

As will be readily appreciated, suitable immunotherapeutic compositions include recombinant (e.g., naked DNA, RNA, viral, bacterial) expression system that encode the treatment relevant neoepitopes, a recombinant immune competent cell (e.g., NK cell, T cell, dendritic cell) expressing the treatment relevant neoepitopes, a recombinant immune competent cell expressing a (chimeric) receptor for the treatment relevant neoepitopes (e.g., T cell expressing CAR), a synthetic antibody for binding the treatment relevant neoepitopes, and a population of white blood cells ex vivo activated with the treatment relevant neoepitopes.

For example, upon selection of treatment relevant neoepitopes, a recombinant nucleic acid can be constructed for intracellular expression and subsequent presentation of the neoepitopes on the cell. The recombinant nucleic acid comprises sequence portions that encode one or more patient- and cancer-specific neoepitopes in an arrangement such that the neoepitope is directed to MHC-I and/or MHC-II presentation pathways and MHC sub-type(s) for which the neoepitope is known to have high affinity. Such targeted and rational-based presentation is thought to produce a more robust immune response, which may be further augmented by subcutaneous delivery or more typically expression of one or more co-stimulatory molecules and/or checkpoint inhibitors. Of course, it should be appreciated that all manners of delivery of such recombinant nucleic acid(s) are deemed suitable and that the recombinant nucleic acid(s) may be formulated as a DNA vaccine, as a recombinant viral genome, or a DNA or RNA deliverable in a transfection composition. Therefore, it is noted that all expression systems known in the art are deemed suitable for use herein (e.g., bacterial expression systems, yeast expression systems, 'naked' DNA and RNA expression systems).

However, it is especially preferred to use viruses already established in gene therapy, including adenoviruses, adeno-associated viruses, alphaviruses, herpes viruses, lentiviruses, etc. However, among other appropriate choices, adenoviruses are particularly preferred. Moreover, it is further generally preferred that the virus is a replication deficient and non-immunogenic virus, which is typically accomplished by targeted deletion of selected viral proteins (e.g., E1, E3 proteins). Such desirable properties may be further enhanced by deleting E2b gene function, and high titers of recombinant viruses can be achieved using genetically modified human 293 cells as has been recently reported (e.g., *J Virol* 1998 February; 72(2): 926-933). Most typically, the desired nucleic acid sequences (for expression from virus infected cells) are under the control of appropriate regulatory elements well known in the art.

With respect to the integration of sequence portions that encode the neoepitopes it should be noted that the various neoepitopes may be arranged in numerous manners, and that a transcription or translation unit may have concatemeric arrangement of multiple epitopes, typically separated by short linkers (e.g., flexible linkers having between 4 and 20 amino acids), which may further include protease cleavage sites. Such concatemers may include between 1 and 20 neoepitopes (typically limited by size of recombinant nucleic acid that can be delivered via a virus), and it should be noted that the concatemers may be identical for delivery to the MHC-I and MHC-II complex, or different. Therefore, and as noted below, it should be appreciated that various peptides can be routed to specific cellular compartments to so achieve preferential or even specific presentation via MHC-I and/or MHC-II. Viewed from another perspective, it should be recognized that tumor associated antigens and neoepitopes may be presented via both presentation pathways, or selectively to one or another pathway at the same time or in subsequent rounds of treatment.

With respect to the 'payload' of the genetically modified virus it is contemplated that expression of more than one treatment relevant neoepitope is preferred, for example two, three, four, five, and even more, which can be accomplished using multiple distinct modified viruses, or a virus having more than one neoepitope sequence (e.g., as concatemeric or chimeric sequence). While not limiting to the inventive subject matter, it is generally preferred that neoepitope sequences are configured as a tandem minigene (e.g., $aa_{12}$-neoepitope$_{12}$-$aa_{12}$), or as single transcriptional unit, which may or may not be translated to a chimeric protein. Thus, it should be appreciated that the epitopes can be presented as monomers, multimers, individually or concatemeric, or as hybrid sequences with N- and/or C-terminal peptides. Most typically, it is preferred that the nucleic acid sequence is back-translated using suitable codon usage to accommodate the virus and/or host codon preference. However, alternate codon usage or non-matched codon usage is also deemed appropriate. With respect to further suitable configurations and expression cassettes reference is made to co-pending US provisional applications with the Ser. No. 62/302,168, filed Mar. 2, 2016, and the Ser. No. 62/314,366, filed Mar. 28, 2016, incorporated by reference herein.

It should be further appreciated that neoepitope sequences (e.g., expressed as single neoepitope or as polytope) may be configured and directed to one or both MEW presentation pathways using suitable sequence elements. With respect to routing the so expressed neoepitopes to the desired MHC-system, it is noted that the MHC-I presented peptides will typically arise from the cytoplasm via proteasome processing and delivery through the endoplasmatic reticulum. Thus, expression of the epitopes intended for MHC-I presentation will generally be directed to the cytoplasm as is further discussed in more detail below. On the other hand, MHC-II presented peptides will typically arise from the endosomal and lysosomal compartment via degradation and processing by acidic proteases (e.g., legumain, cathepsin L and cathepsin S) prior to delivery to the cell membrane. Thus, expression of the epitopes intended for MHC-II presentation will generally be directed to the endosomal and lysosomal compartment as is also discussed in more detail below.

In most preferred aspects, signal peptides may be used for trafficking the neoepitopes to the endosomal and lysosomal compartment (and with directing the neoepitope presentation towards MHC-II), or for retention in the cytoplasmic space (and with directing the neoepitope presentation towards MHC-I). For example, where the peptide is to be exported to the endosomal and lysosomal compartment targeting presequences and the internal targeting peptides can be employed. The presequences of the targeting peptide are preferably added to the N-terminus and comprise between 6-136 basic and hydrophobic amino acids. In case of peroxisomal targeting, the targeting sequence may be at the C-terminus. Other signals (e.g., signal patches) may be used and include sequence elements that are separate in the peptide sequence and become functional upon proper peptide folding. In addition, protein modifications like glycosylations can induce targeting. Among other suitable targeting signals, the inventors contemplate peroxisome targeting signal 1 (PTS1), a C-terminal tripeptide, and peroxisome targeting signal 2 (PTS2), which is a nonapeptide located near the N-terminus. In addition, sorting of proteins to endosomes and lysosomes may also be mediated by signals within the cytosolic domains of the proteins, typically comprising short, linear sequences. Some signals are referred to as tyrosine-based sorting signals and conform to the NPXY or YXXØ consensus motifs. Other signals known as dileucine-based signals fit [DE]XXXL[L1] or DXXLL consensus motifs. All of these signals are recognized by components of protein coats peripherally associated with the cytosolic face of membranes. YXXO and [DE]XXXL[L1] signals are recognized with characteristic fine specificity by the adaptor protein (AP) complexes AP-1, AP-2, AP-3, and AP-4, whereas DXXLL signals are recognized by another family of adaptors known as GGAs. Also FYVE domain can be added, which has been associated with vacuolar protein sorting and endosome function. In still further aspects, endosomal compartments can also be targeted using human CD1 tail sequences (see e.g., *Immunology*, 122, 522-531).

Trafficking to or retention in the cytosolic compartment may not necessarily require one or more specific sequence elements. However, in at least some aspects, N- or C-terminal cytoplasmic retention signals may be added, including a membrane-anchored protein or a membrane anchor domain of a membrane-anchored protein. For example, membrane-anchored proteins include SNAP-25, syntaxin, synaptoprevin, synaptotagmin, vesicle associated membrane proteins (VAMPs), synaptic vesicle glycoproteins (SV2), high affinity choline transporters, Neurexins, voltage-gated calcium channels, acetylcholinesterase, and NOTCH.

Additionally, it is contemplated that the viral delivery vehicle also encodes at least one, more typically at least two, eve more typically at least three, and most typically at least four co-stimulatory molecules to enhance the interaction between the infected dendritic cells and T-cells. For example, suitable co-stimulatory molecules include ICAM-1 (CD54), ICOS-L, and LFA-3 (CD58), especially in combination with B7.1 (CD80) and/or B7.2 (CD86). Further contemplated co-stimulatory molecules include 4-1BBL, CD30L, CD40, CD40L, CD48, CD70, CD112, CD155, GITRL, OX40L, and TL1A. Moreover, it should be appreciated that expression of the co-stimulatory molecules will preferably be coordinated such that the antigens and/or neoepitopes are presented along with one or more co-stimulatory molecules. Thus, it is typically contemplated that the co-stimulatory molecules are produced from a single transcript, for example, using an internal ribosome entry site or 2A sequence, or from multiple transcripts.

Likewise, it is contemplated that the viral vector will further include a sequence portion that encodes one or more peptide ligands that bind to a checkpoint receptor. Most typically, binding will inhibit or at least reduce signaling via the receptor, and particularly contemplated receptors include CTLA-4 (especially for CD8+ cells) and PD-1 (especially for CD4+ cells). For example, peptide binders can include antibody fragments and especially scFv, but also small molecule peptide ligands that specifically bind to the receptors. Once more, it should be appreciated that expression of the peptide molecules will preferably be coordinated such that the antigens and/or neoepitopes are presented along with one or more peptide molecules. Thus, it is typically contemplated that the peptide molecules are produced from a single transcript, for example, using an internal ribosome entry site or 2A sequence, or from multiple transcripts.

Viruses may then be individually or in combination used as a therapeutic vaccine in a pharmaceutical composition, typically formulated as a sterile injectable composition with a virus titer of between $10^4$-$10^{11}$ virus particles per dosage unit. Alternatively, the virus may be employed to infect patient (or other HLA matched) cells ex vivo and the so infected cells are then transfused to the patient. In further examples, treatment of patients with the virus may be accompanied by allografted or autologous natural killer cells or T cells in a bare form or bearing chimeric antigen receptors expressing antibodies targeting neoepitope, neoepitopes, tumor associated antigens or the same payload as the virus. The natural killer cells, which include the patient-derived NK-92 cell line, may also express CD16 and can be coupled with an antibody. As used herein, the term "administering" a pharmaceutical composition or immunotherapeutic composition refers to both direct and indirect administration of the composition, wherein direct administration of the composition is typically performed by a health care professional (e.g., physician, nurse, etc.), and wherein indirect administration includes a step of providing or making available the pharmaceutical composition or drug to the health care professional for direct administration (e.g., via injection, infusion, oral delivery, topical delivery, etc.).

In further contemplated aspects, immunotherapeutic compositions may also include one or more of the treatment relevant neoepitopes, typically prepared as a synthetic peptide. There are numerous methods known in the art to prepare synthetic peptides, and all known manners are deemed suitable for use herein. For example, peptides with cancer neoepitope sequences can be prepared on a solid phase (e.g., using Merrifield synthesis), via liquid phase synthesis, or from smaller peptide fragments. In less preferred aspects, peptides could also be produced by expression of a recombinant nucleic acid in a suitable host (especially where multiple treatment relevant neoepitopes are on a single peptide chain, optionally with spacers between neoepitopes or cleavage sites).

Therefore, the structure of the synthetic peptides corresponding to or comprising the treatment relevant neoepitope sequences may be X-$L_1$-($A_n$-$L_2$)$_m$-Q, in which X is an optional coupling group or moiety that is suitable to covalently or non-covalently attaches the synthetic peptide to a solid phase, $L_1$ is an optional linker that covalently links the synthetic peptide to a solid phase or the coupling group. An is the synthetic peptide having the neoepitope sequence with A being a natural (proteinogenic) amino acid and n is an integer between 7 and 30, and most typically between 7 and 11 or 15-25. $L_2$ is an optional linker that may be present, especially where multiple synthetic peptide sequences (identical or different) are in the construct, and m is an integer, typically between 1 and 30, and most typically between 2 and 15. Finally, Q is a terminal group which may used to couple the end of the synthetic peptide to the solid phase (e.g., to sterically constrain the peptide) or to a reporter group (e.g., fluorescence marker) or other functional moiety (e.g., affinity marker). Consequently, it should be noted that where the synthetic peptide is used for direct MHC-I binding, the overall length will be between 8 and 10 amino acids. Similarly, where the synthetic peptide is used for direct MHC-II binding, the overall length will be between 14 and 20 amino acids. On the other hand, where the synthetic peptide is processed in the cell (typically via proteasome processing) prior to MHC presentation, the overall length will typically be between 10 and 40 amino acids, with the changed amino at or near a central position in the synthetic peptide.

For example, X could be a non-covalent affinity moiety (e.g., biotin) that binds a corresponding binding agent (e.g., avidin) on the solid phase, or a chemical group (with or without spacer) that reacts with the N- or C-terminal amino or carboxyl group of the peptide, or a selectively reactive group (e.g., iodoacetyl or maleimide group) that reacts with a sulfhydryl group in the peptide or linker $L_1$. $L_1$ may be used to increase the distance of the synthetic peptide from the solid phase and will therefore typically comprise a flexible linear moiety (e.g., comprising glycol groups, alkoxy groups, glycine, etc.) having a length of equivalent to between about 2-20 carbon-carbon bonds (e.g., between 0.3 nm and 3 nm). Of course, it should also be appreciated that the synthetic peptide may use the solid phase on which the peptide was produced and as such not require a separate coupling group or linker.

Depending on the particular synthetic peptide and coupling method, it should be appreciated that the nature of the solid phase may vary considerably, and all known solid phases for attachment of peptides are deemed suitable for use herein. For example, suitable solid phases include agarose beads, polymer beads (colored or otherwise individually addressable), wall surfaces of a well in a microtiter plate, paper, nitrocellulose, glass, etc. The person of ordinary skill in the art will be readily appraised of a suitable choice of solid phase and attachment chemistry. In further preferred aspects, it is also noted that the solid phase will generally be suitable for protocols associated with phage display methods such as to allow peptides presented on a phage (or other scaffold carrier) to reversibly bind to the solid phase via the synthetic peptide. In still further contemplated uses, it should also be recognized that the solid phase may be a carrier protein used in vaccination (e.g., albumin, KLH, tetanus toxoid, diphtheria toxin, etc.), particularly where the synthetic protein is used as a vaccine in a mammal or as an immunogenic compound in a non-human mammal for antibody production. Likewise, the synthetic protein may also be used as a vaccine or immunogenic compound without any carrier.

To obtain a synthetic antibody against the identified treatment relevant neoepitope(s), it is contemplated that the in silico indentified is prepared in vitro to yield a synthetic peptide. In still further preferred methods, it should be recognized that where the synthetic peptide (that comprises or corresponds to the cancer neoepitope) is immobilized on a solid phase, affinity agents, and particularly antibodies, to the neoepitope may be isolated and/or refined. Most preferably, such isolation will include a prefabricated high-diversity library of antibodies. As used herein, and unless the context dictates otherwise, the term "antibody" or "antibodies" includes all isotypes and subtypes of antibodies (e.g., IgG, IgM, IgE, etc.) as well as all fragments thereof, including monovalent IgG, F(ab')$_2$, Fab', Fab, scFv, scFv-Fc, VhH, etc. Moreover, contemplated antibodies may be humanized, of human or non-human (e.g., rodent) origin, or may be chimeric. In a typical method, a high-diversity library may be a phage display library having a diversity of at least $10^9$ diverse members, or at least $10^{10}$ diverse members, or even higher, typically based on M13 phages and display via pIII, pVIII, pVI, or pIX, or based on T7 phages and the gene 10 capsid protein. As should be readily appreciated, use of large diversity libraries will provide in relatively short time several binding candidate antibodies that can be further selected for best binders. Indeed, where binding affinity to the immobilized synthetic peptide is less than desired, it should be recognized that affinity can be improved via affinity maturation using protocols well known in the art. For example, low affinity ($K_D>10^{-7}$M) binders or members of smaller libraries may be subjected to affinity maturation to improve binding affinity and/or kinetic using methods well known in the art (see e.g., *Briefings In Functional Genomics And Proteomics*. Vol 1. No 2.189-203. July 2002). In addition, it should be noted that while antibody libraries are generally preferred, other scaffolds are also deemed suitable and include beta barrels, ribosome display, cell surface display, etc. (see e.g., *Protein Sci*. 2006 January; 15(1): 14-27.) Thus, it should be appreciated that in preferred aspects the synthetic peptide is used as a bait in a library of antibodies to so identify high-affinity binding ($K_D<10^{-7}$M, and more typically $K_D<10^{-8}$M) antibodies.

As the antibodies are directly coupled to the cell that carries the nucleic acid encoding these antibodies, it should be further appreciated that such nucleic acid can then be analyzed to identify sequence elements encoding the hypervariable loops, the CDR1, CDR2, and CDR3, for light and heavy chain, respectively, and/or SDRs (specificity determining residues). Most typically, determination is performed using standard sequencing methods. Once determined, it is then contemplated that the hypervariable loops, or the CDR1-H, CDR2-H, and/or CDR3-H and/or the CDR1-L, CDR2-L, and/or CDR3-L, and/or SDRs are grafted onto a human or humanized antibody scaffold or antibody. As will be readily appreciated, grafting can be done by genetic engineering of a nucleic acid that encodes the human or humanized antibody scaffold or antibody. For example, within each CDR, there are more variable positions that are directly involved in the interaction with antigen, i.e., specificity-determining residues (SDRs), whereas there are more conserved residues that maintain the conformations of CDRs loops. SDRs may be identified from the 3D structure of the antigen-antibody complex and/or the mutational analysis of the CDRs. An SDR-grafted humanized antibody is constructed by grafting the SDRs and the residues maintaining the conformations of the CDRs onto human template. Consequently, it should be recognized that human or humanized antibodies with specificity to cancer neoepitopes can be prepared in an entirely synthetic manner in which the antibody is expressed in a cell that has not previously contacted the antigen. Moreover, contemplated methods allow production of patient and cancer specific antibodies for treatment of a patient that has failed to produce or effectively use antibodies against the treatment relevant neoepitopes.

While not limiting to the inventive subject matter, so prepared synthetic antibodies can be used directly as an IgG (or other isotype), as a fragment (e.g., bispecific Fab or other bispecific fragment), and/or as a chimeric protein (e.g., scFv as ectodomain in a chimeric T cell receptor), alone or in conjugation with a therapeutic or diagnostic agent, and/or as a hybrid protein with a transmembrane domain to ensure membrane anchoring of the antibody to a cell. Thus, the inventors contemplate a method of generating an immunotherapeutic composition for cancer immune therapy in which the so identified synthetic antibodies are coupled to a therapeutic or diagnostic agent (which may have a cellular or non-cellular component) to so obtain the immunotherapeutic composition.

Regardless of the particular type of the immunotherapeutic composition, it should be recognized that the determination of treatment relevant neoepitopes can be iteratively done after first and/or successive rounds of treatment (which may include surgery, immunotherapy, radiation, chemotherapy, etc.). Most typically, the so obtained info on the newly identified treatment relevant neoepitopes may be used in further immunotherapy (e.g., recombinant adenovirus, or synthetic antibodies, possibly in combination with modified NK cells, all optionally in conjunction with checkpoint inhibitors). Moreover, it is generally contemplated that where immunotherapy is employed, conventional chemotherapy treatment may be performed at a relatively low dose to support or maintain immune function. For example chemotherapy may be performed using a low-dose regime (e.g., between 0.1% and 1%, or 1% and 5%, or 5% and 10%, or 10% and 20%, or higher but less than 50%, or less than 60% or less than 75% of conventional (see prescribing info) dosage).

Duration of treatment cycles comprising immunotherapy and/or chemotherapy (or other therapeutic interventions) will typically depend on the type and stage of cancer, the type of drug, and/or health of the patient, and it should be appreciated that multiple rounds of administrations of drugs may required that are separated by hours to days or even weeks. Thus, treatment cycles will typically last at least one day, more typically at least one week, even more typically at least 4 weeks, most typically at least 6 weeks. Viewed from a different perspective, the duration of a treatment cycle may be between 1 week and 1 month, between 1 month and 3 moths, or between 6 weeks and 6 months, or even longer (e.g., until remission, or other diagnostic end point). Upon conclusion of a treatment cycle, a traditional evaluation (e.g., using radiographic, hematologic, or other test) is typically performed and will be complemented by at least one new set of biopsies, typically including at least some of the same locations as in the first or prior round. Of course, as needed, new locations may also be sampled. Where a therapy has been effective, and where the primary tumor and/or metastases are undetectable or unsuitable for biopsy, it is contemplated that circulating tumor cells (CTC) or microvesicles or exosomes may be isolated and analyzed for further omics information to evaluate treatment progress and/or efficacy. For example, the treatment may be effective to halt metastases and CTC, but not growth of the primary tumor; or treatment may be effective for the primary tumor but not for all or some metastases. Depending on the outcome of the evaluation and/or omics information, immunotherapy or chemotherapy may be adapted accordingly. For example, new sets of neoepitopes may be targeted where prior epitopes persist. A change in omics data may be indicative of an evolutionary shift in a population of cancer cells, and a shift to a specific cell or epitope population may indicate suitability of particular treatment or exclude other treatment options.

For example, a new round of immunotherapy and/or chemotherapy is performed as, or in a similar fashion as the initial or previous round, and will be informed by the determined first and/or second (and/or subsequent) set of treatment relevant neoepitopes. Therefore, the second round of treatment will typically be different from first in terms of treatment relevant neoepitopes, but may also be different in terms of the type of treatment (e.g., using a different adenovirus, a different set of antibodies or synbodies, or use of different NK cells (e.g., NK-92 modified cells carrying antibodies against neoepitopes, etc.)). It is thus contemplated that subsequent rounds of biopsies and further modified or otherwise adapted immunotherapy or chemotherapy will help reduce or maintain cancer growth or eliminate the tumor altogether. Alternatively or additionally, antibodies against neoepitopes may be used as targeting entities using NK cells, and especially NK-92 cells (that may be further modified to exhibit a high affinity Fc-cell receptor). In further contemplated aspects of the inventive subject matter, the antibody fragment or antibody may also be bound to a T-cell, and especially to a NK-cell to so stimulate and direct an immune response to the cells displaying the neoepitope. Consequently, it should be recognized that an effective immune response against a cancer neoepitope may be elicited using a process that does not require immunization in the patient or other organism, reducing dramatically response time and availability of therapeutic antibodies.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary. Moreover, all methods described herein can be performed in any suitable order unless otherwise indicated herein or otherwise clearly contradicted by context.

The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A computer-assisted method of making an immunotherapeutic composition, the method comprising:
    obtaining, from a patient, omics data from a tumor tissue, and comparing, via at least one processor, digital omics data stored in a computer-readable memory for tumor cells in a first location in a patient to omics data for tumor cells in a second location in the patient to identify respective DNA sequences that encode neoepitopes in the tumor cells of the first and second locations, wherein the omics data comprise whole genome DNA sequencing data or whole exome DNA sequencing data, and wherein the first and second locations are anatomically different locations, and wherein the neoepitopes are peptide sequences having a length of between 5 and 30 amino acids, and wherein the neoepitopes include a mutation in peptide sequences relative to an amino acid sequence from matched normal omics data from the patient;
    determining, via the at least one processor, from a patient sample or the matched normal omics data, an HLA type of the patient;
    calculating, via the at least one processor, for the neoepitopes respective binding affinities with respect to the determined HLA type of the patient;
    selecting, via the at least one processor, high-affinity neoepitopes for the first and second locations that have a binding affinity to the determined HLA type of the patient of less than 500 nM;
    selecting, from the high-affinity neoepitopes at least in part via the at least one processor, target neoepitopes for the first and second locations such that the target neoepitopes for the first and second locations have the same attribute, wherein the attribute is selected from the group consisting of a group attribute, a location attribute, a function attribute, a metabolic attribute, and a pathway attribute; and
    generating an immunotherapeutic composition prepared for administration, the composition comprising a neoepitope-specific cell based composition, wherein the neoepitope-specific cell based composition comprises an immune competent cell that is genetically modified to express a chimeric antigen receptor that specifically recognizes or binds to the at least one of the target neoepitopes to target tumor cells in the first and second locations that express the target neoepitopes.

2. The method of claim 1 wherein the omics data have a BAMBAM format, a SAMBAM format, a FASTQ format, or a FASTA format.

3. The method of claim 1 wherein the neoepitopes in the comparing step are determined in silico by a process that performs a location-guided synchronous alignment of omics data for the tumor cells and matched normal omics data.

4. The method of claim 1 wherein the first location is a primary tumor and where the second location is selected from the group consisting of a locoregional metastasis, a distant metastasis, a lymph node, and a circulatory system.

5. The method of claim 1 further comprising a step of confirming expression of the high-affinity neoepitopes.

6. The method of claim 1 wherein the group attribute is selected from the group consisting of a unique neoepitope, a shared neoepitope, ploidy status, and clonality status.

7. The method of claim 1 wherein the location attribute is selected from the group consisting of primary tumor location, a metastasis location, and a circulatory system.

8. The method of claim 1 wherein the function attribute is selected from the group consisting of a driver mutation, a passenger mutation, and methylation status.

9. The method of claim 1 wherein the metabolic attribute is selected from the group consisting of drug resistance and increased glycolysis.

10. The method of claim 1 wherein the pathway attribute is selected from the group consisting of a mutation in a growth signaling pathway, a mutation in an apoptosis signaling pathway, a mutation in a hormonal signaling pathway, and a shift in signaling pathway usage.

11. The method of claim 1 wherein the HLA type of the patient is determined from the matched normal omics data.

12. The method of claim 1 wherein the HLA type of the patient is determined to at least 4-digit depth.

13. The method of claim 1 wherein the binding affinity of the high-affinity neoepitopes to the determined HLA type of the patient is less than 250 nM.

14. The method of claim 1 wherein the immune competent cell is a genetically modified NK cell or a genetically modified T cell.

15. The method of claim 1 wherein the patient was previously treated with an initial immunotherapeutic composition that is different from the immunotherapeutic composition.

16. The method of claim 1 wherein the patient was previously treated with chemotherapy.

17. A method of treating a tumor with an immunotherapeutic composition, the method comprising:
    preparing the immunotherapeutic composition by the steps of:
        comparing omics data for tumor cells in a first location in a patient to omics data for tumor cells in a second location in the patient to identify respective DNA sequences that encode neoepitopes in the tumor cells of the first and second locations, wherein the omics data comprise whole genome DNA sequencing data or exome DNA sequencing data, and wherein the first and second locations are anatomically different locations, and wherein the neoepitopes are peptide sequences having a length of between 5 and 30 amino acids, and wherein the neoepitopes include a mutation in peptide sequences relative to an amino acid sequence from matched normal omics data from the patient;
        determining from a patient sample or the matched normal omics data, an HLA type of the patient;
        calculating for the neoepitopes respective binding affinities with respect to the determined HLA type of the patient;

selecting high-affinity neoepitopes for the first and second locations that have a binding affinity to the determined HLA type of the patient of less than 500 nM;

selecting, from the high-affinity neoepitopes, target neoepitopes for the first and second locations such that the target neoepitopes for the first and second locations have the same attribute, wherein the attribute is selected from the group consisting of a group attribute, a location attribute, a function attribute, a metabolic attribute, and a pathway attribute; and generating an immunotherapeutic composition comprising a neoepitope-specific cell based composition, wherein the neoepitope-specific cell based composition comprises an immune competent cell that is genetically modified to express a chimeric antigen receptor that specifically recognizes or binds to the at least one of the target neoepitopes to target tumor cells in the first and second locations that express the target neoepitopes;

treating the tumor by administering to a patient in need thereof the immunotherapeutic composition.

18. The method of claim 17 further comprising a step of administering a new round of immunotherapy or chemotherapy subsequent to the step of administering the immunotherapeutic composition to the patient.

19. The method of claim 18 wherein the new round of immunotherapy or chemotherapy is informed by identification of treatment relevant neoepitopes.

20. The method of claim 17 further comprising a step of administering chemotherapy using a low-dose regime.

* * * * *